United States Patent
Jordanova et al.

(10) Patent No.: US 9,447,391 B2
(45) Date of Patent: Sep. 20, 2016

(54) DIAGNOSTIC TESTS FOR THE DETECTION OF INHERITED PERIPHERAL NEUROPATHIES

(71) Applicants: VIB VZW, Ghent (BE); UNIVERSITEIT ANTWERPEN, Antwerp (BE)

(72) Inventors: Albena Jordanova, Edegem (BE); Magdalena Zimon, Antwerp (BE); Jonathan Baets, Antwerp (BE); Peter De Jonghe, Mechelen (BE)

(73) Assignees: VIB VZW, Ghent (BE); Universiteit Antwerpen, Antwerp (BE)

( * ) Notice: Subject to any disclaimer, the term of this patent is extended or adjusted under 35 U.S.C. 154(b) by 0 days.

(21) Appl. No.: 14/371,166

(22) PCT Filed: Jan. 10, 2013

(86) PCT No.: PCT/EP2013/050379
§ 371 (c)(1),
(2) Date: Jul. 8, 2014

(87) PCT Pub. No.: WO2013/104701
PCT Pub. Date: Jul. 18, 2013

(65) Prior Publication Data
US 2014/0356871 A1 Dec. 4, 2014

Related U.S. Application Data

(60) Provisional application No. 61/586,514, filed on Jan. 13, 2012.

(51) Int. Cl.
| | | |
|---|---|---|
| *C12Q 1/68* | (2006.01) | |
| *C12P 19/34* | (2006.01) | |
| *C07H 21/02* | (2006.01) | |
| *C07H 21/04* | (2006.01) | |
| *C12N 9/14* | (2006.01) | |

(52) U.S. Cl.
CPC ............. *C12N 9/14* (2013.01); *C12Q 1/6883* (2013.01); *C12Q 2600/156* (2013.01); *C12Y 309/01001* (2013.01)

(58) Field of Classification Search
None
See application file for complete search history.

(56) References Cited

U.S. PATENT DOCUMENTS 6,582,908 B2 * 6/2003 Fodor et al. .............. 506/9
7,217,523 B2 * 5/2007 Wagner .................. 435/6.1

FOREIGN PATENT DOCUMENTS

WO 2013104701 A1 7/2013

OTHER PUBLICATIONS

De Sandre-Giovannoli A. et al., "Homozygous Defects in LMNA, Encoding Lamin A/C Nuclear-Envelope Proteins, Cause Autosomal Recessive Axonal Neuropathy in Human (Charcot-Marie-Tooth Disorder Type 2) and Mouse" American Journal of Human Genetics, vol. 70, No. 3, 2002, pp. 726-736.
Lima, C. D. et al., "Three-dimensional structure of human protein kinase C interacting protein 1, a member of the HIT family of proteins" Proceedings of the National Academy of Sciences, vol. 93, May 1996, pp. 5357-5362.
Ozga, Magdalena et al., "Histidine Triad Nucleotide-binding Protein 1 (HINT-1) Phosphoramidease Transforms Nucleoside 5'-O'-Phosphorothioates to Nucleoside 5'-O'-Phosphates" J. Biol. Chem., vol. 285, No. 52, Dec. 2010, pp. 40809-40818.
Parks, Kristen P. et al., "Altered Specificity of Hint-W123Q supports a role for Hint Inhibition by ASW in avian sex determination" Physiological Genomics, vol. 20, No. 1, Dec. 2004, pp. 12-14.
Rotthier, Annelies et al., "Genes for hereditary sensory and autonomic neuropathies: a genotype-phenotype correlation" Brain, Oxford Univ. Press, vol. 132, Part 10, Oct. 2009, pp. 2699-2711.
Weiske, Jörg et al., "The Histidine Triad Protein Hing1 Triggers Apoptosis Independent of Its Enzymatic Activity" J. Biol. Chem., vol. 281, No. 37, Sep. 20006, pp. 27356-27366.
Zimon, Magdalena et al. "Loss-of-function mutations in HINT1 cause axonal neuropathy with neuromyotonia" Nature Genetics, vol. 44, No. 10, Oct. 2012, pp. 1080-1083.
Genbank sequence NM_005340.5 at http://www.ncbi.nlm.nih.gov/sviewer/viewer.fcgi?db=nuccore&val=NM_005340.3&page_size=5&report=gbwithparts visited on Nov. 12, 2015.

* cited by examiner

*Primary Examiner* — Katherine Salmon
(74) *Attorney, Agent, or Firm* — TraskBritt P.C.

(57) ABSTRACT

The disclosure relates to the field of human genetics, particularly the field of peripheral neuropathy, particularly inherited peripheral neuropathy. Specifically, the disclosure relates to methods and materials to detect hereditary peripheral neuropathy, more particularly autosomal recessive Charcot-Marie-Tooth disease.

4 Claims, 2 Drawing Sheets

Figure 1

Figure 2

SEQUENCE LISTING

<160> NUMBER OF SEQ ID NOS: 2

<210> SEQ ID NO 1
<211> LENGTH: 782
<212> TYPE: DNA
<213> ORGANISM: Homo sapiens

<400> SEQUENCE: 1

| | | | | | |
|---|---|---|---|---|---|
| acgcgcaaga | ttaggtgggg | cgccagagcc | ggggcacctg | cgcaggcttg | gctgcgccct | 60 |
| ctcgcgccgc | acgctctgcg | ggttcctccc | ttcttccgag | cctctcctct | ggccgccgcg | 120 |
| cgggagagag | gccgagatgg | cagatgagat | tgccaaggct | caggtcgctc | ggcctggtgg | 180 |
| cgacacgatc | tttgggaaga | tcatccgcaa | ggaaatacca | gccaaaatca | ttttgagga | 240 |
| tgaccggtgc | cttgctttcc | atgacatttc | ccctcaagca | ccaacacatt | ttctggtgat | 300 |
| acccaagaaa | catatatccc | agatttctgt | ggcagaagat | gatgatgaaa | gtcttcttgg | 360 |
| acacttaatg | attgttggca | agaaatgtgc | tgctgatctg | ggcctgaata | agggttatcg | 420 |
| aatggtggtg | aatgaaggtt | cagatggtgg | acagtctgtc | tatcacgttc | atctccatgt | 480 |
| tcttggaggt | cggcaaatgc | attggcctcc | tggttaagca | cgttttgggg | ataattttct | 540 |
| cttctttagg | caatgattaa | gttaggcaat | ttccagtatg | ttaagtaaca | cacttatttt | 600 |
| tgcctgtgta | tggagagatt | caagaaataa | ttttaaaacc | gcatacataa | taaaagacat | 660 |
| tgttgcatgg | cttatagtct | ctctgagtgt | tgcgtttgat | ttgttatttt | aaaaacatat | 720 |
| ttgttggaat | atgtgaaggt | gggtttataa | ttttggatgt | ttcttgcttt | ttcttcccaa | 780 |
| gg | | | | | | 782 |

<210> SEQ ID NO 2
<211> LENGTH: 126
<212> TYPE: PRT
<213> ORGANISM: Homo sapiens

<400> SEQUENCE: 2

Met Ala Asp Glu Ile Ala Lys Ala Gln Val Ala Arg Pro Gly Gly Asp
1               5                   10                  15

Thr Ile Phe Gly Lys Ile Ile Arg Lys Glu Ile Pro Ala Lys Ile Ile
            20                  25                  30

Phe Glu Asp Asp Arg Cys Leu Ala Phe His Asp Ile Ser Pro Gln Ala
        35                  40                  45

Pro Thr His Phe Leu Val Ile Pro Lys Lys His Ile Ser Gln Ile Ser
    50                  55                  60

Val Ala Glu Asp Asp Glu Ser Leu Leu Gly His Leu Met Ile Val
65                  70                  75                  80

Gly Lys Lys Cys Ala Ala Asp Leu Gly Leu Asn Lys Gly Tyr Arg Met
                85                  90                  95

Val Val Asn Glu Gly Ser Asp Gly Gly Gln Ser Val Tyr His Val His
            100                 105                 110

Leu His Val Leu Gly Gly Arg Gln Met His Trp Pro Pro Gly
        115                 120                 125

DIAGNOSTIC TESTS FOR THE DETECTION OF INHERITED PERIPHERAL NEUROPATHIES

CROSS-REFERENCE TO RELATED APPLICATIONS

This application is a national phase entry under 35 U.S.C. §371 of International Patent Application PCT/EP2013/050379, filed Jan. 10, 2013, designating the United States of America and published in English as International Patent Publication WO2013/104701 A1 on Jul. 18, 2013, which claims the benefit under Article 8 of the Patent Cooperation Treaty and 35 U.S.C. §119(e) to U.S. Application Ser. No. 61/586,514, filed Jan. 13, 2012.

TECHNICAL FIELD

The disclosure relates generally to biotechnology and more particularly to defects in HINT1 associated with peripheral neuropathy, more particularly peripheral neuropathy associated with neuromyotonia. Accordingly, the disclosure provides assays and a diagnostic test for the identifying an individual suspected of having peripheral neuropathy or being a carrier of a peripheral neuropathy mutation.

BACKGROUND

Inherited Peripheral Neuropathies (IPN) form a clinically diverse group of disorders affecting 1 in 2500 individuals[1]. The most common type is Charcot-Marie-Tooth disease (CMT), a sensorimotor neuropathy causing progressive distal muscle atrophy, weakness and sensory loss. Autosomal dominant, autosomal recessive (AR) and X-linked forms of IPN are representing a genetic spectrum of at least 50 causal genes. Even after subdivision in specific phenotypes, IPN are genetically heterogeneous. Although striking clinical features may be of particular use to distinguish genetic subtypes and guide diagnostic screening, many families remain without molecular diagnosis suggesting the existence of unknown causes. Our understanding of these disorders has progressed from the description of the clinical phenotypes and delineation of the electrophysiological and pathological features to the identification of disease genes and elucidation of the underlying molecular mechanisms. Recent molecular analysis of the inherited peripheral neuropathies (IPN) has led to important insights into the process of myelination and the function of some of the genes involved. An important problem for the physician is that the IPN show considerable clinical and genetic heterogeneity. The discovery that mutations in multiple genes result in similar phenotypes argues for complex protein interactions and complementing functions for each protein product within the nerve tissue. Knowledge of the structure and function of the causal genes is currently being actively pursued to better classify peripheral neuropathies and to elucidate the underlying molecular mechanisms of these diseases. Thus, the knowledge of the exact genetic aberration in the patients has important ramifications for diagnosis, prognosis, genetic counseling, and approaches for therapy.

BRIEF SUMMARY

In the disclosure we have identified loss of function mutations in the HINT1 protein associated with inherited peripheral neuropathies, more particularly with an autosomal recessive axonal neuropathy, in particularly an autosomal recessive axonal neuropathy associated with neuromyotonia. The disclosure can be used for the manufacture of a diagnostic assay for a more correct diagnosis of inherited peripheral neuropathies.

DETAILED DESCRIPTION

In order to facilitate review of the various embodiments of the disclosure and provide an understanding of the elements and constituents used in making and using the disclosure, the following terms used in the disclosure description have the meanings as defined below. In addition, unless otherwise noted, technical terms are used according to conventional usage. Definitions of common terms in molecular biology may be found in Benjamin Lewin, Genes IX, published by Oxford University Press, 2007; Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). In addition, it is readily apparent to one skilled in the art that various embodiments and modifications may be made to the disclosure disclosed in this application without departing from the scope and spirit of the disclosure.

The disclosure provides mutations in the histidine triad nucleotide binding protein 1 (HINT1) causing peripheral neuropathy, particularly autosomal-recessive inherited peripheral neuropathy, more particularly autosomal-recessive inherited peripheral neuropathy associated with neuromyotonia. In one embodiment, the mutations lead to a loss of function of the HINT1 gene product. In a particular embodiment, the one or more mutations present in the HINT1 gene result in a reduced biological activity of HINT1 or in a reduced expression (e.g., reduced mRNA production of HINT1 or a reduced HINT1 protein expression) of HINT1. With the wording "a reduced function of HINT1" it is meant that with respect to the function of the wild-type HINT1, the mutant HINT1 protein has less than 50%, less than 40%, less than 30%, less than 20%, less than 10% or even lower activity. The activity of HINT1 can be measured in an enzymatic assay as, for example, described in Bieganowski P. et al. (2002) *J. Biological Chemistry* 277, pp. 10852-10860. Alternatively, the activity of HINT1 can be measured in a yeast complementation assay as described in Bieganowski P. et al. (2002) *J. Biological Chemistry* 277, pp. 10852-10860.

In yet another embodiment, the one or more mutations can lead to a truncated mRNA encoding HINT1. In yet another embodiment, the one or more mutations can lead to a truncated polypeptide of HINT1, thus a fragment of the HINT1 polypeptide, which is smaller than the polypeptide depicted in SEQ ID NO:2.

The terms "neuropathy" or "neuropathies," as used herein, is defined as a functional defect or defects and/or a pathological change or changes in the peripheral nervous system. In a specific embodiment, the peripheral neuropathy is an autosomal recessive form of the Charcot-Marie-Tooth (CMT) syndrome. In yet another particular embodiment, the peripheral neuropathy is an autosomal recessive axonal peripheral neuropathy associated with the presence of neuromyotonia.

Histidine triad nucleotide-binding protein 1 (HINT1) is an ubiquitously expressed homodimeric purine phosphoramidase capable of hydrolyzing substrates as, for example, lysyl-tRNA synthetase-generated lysyl-AMP[3-5]. Additionally, HINT1 was shown to be a tumor suppressor, participating in several apoptotic pathways[6,7]. In addition, we found HINT1 to be expressed at high levels in mouse sciatic nerve.

The human HINT1 gene is located at chromosome 5q31.1 and its sequence is available in GenBank (Accession Number NM_005340.5, its protein sequence has the Accession Number NP_005331.1). Alternative names of the histidine triad nucleotide binding protein 1 are protein kinase C inhibitor, Protein kinase C-interacting protein, or adenosine 5'-monophosphoramidase. In the disclosure the gene sequence of HINT1 is depicted in SEQ ID NO:1 and the protein sequence is depicted in SEQ ID NO:2.

The disclosure shows that mutations in the HINT1 gene encoding for a HINT1 protein product with a loss of enzymatic function of HINT1 or a reduced loss of function of HINT1 or compromised protein stability, in both alleles of HINT1, is associated with the presence of peripheral neuropathy or the predisposition to peripheral neuropathy in a subject. The identification of a role for HINT1 in peripheral neuropathy opens new avenues for the diagnosis of peripheral neuropathies, more particularly autosomal recessive axonal neuropathy, even more particularly autosomal recessive axonal neuropathy associated with neuromyotonia.

In a first embodiment, the disclosure provides an isolated nucleic acid coding for a mutant HINT1 polypeptide, the nucleic acid containing in comparison to the wild-type HINT1 encoding sequence set forth in SEQ ID NO:1 one or more mutations wherein the presence of the nucleic acids leads to a loss of function of the protein HINT1, which sequence is set forth in SEQ ID NO:2. In yet another embodiment, the disclosure provides an isolated nucleic acid coding for a mutant HINT1 polypeptide, the nucleic acid containing in comparison to the wild-type HINT1 encoding sequence set forth in SEQ ID NO:1 one or more mutations selected from the mutations set forth in Table 1.

"Mutant," as used herein, refers to a HINT1 gene that either does not express any detectable protein product or to a HINT1 gene that expresses a non-functional protein product or expresses a HINT1 protein with a reduced function as compared to the wild-type HINT1. Non-limiting examples of such mutations are mutations which are depicted in Table 1. Thus, the HINT1 mutant alleles, which have been identified, lead to a loss of function of HINT1 or to a reduced function of HINT1. In a particular aspect no HINT1 protein is detectably made from the mutant allele. With respect to the HINT1 gene of the disclosure, the term "mutant" refers to a gene encoding HINT1, bearing one or more nucleotide substitutions, insertions, deletions and/or duplications, which lead to the development of a peripheral neuropathy or to a predisposition of peripheral neuropathy, more particularly an autosomal recessive form of an inherited peripheral neuropathy when expressed in humans. In a specific embodiment, the HINT1 mutation(s) is (are) present in a homozygous form (i.e., both alleles carry the same mutation or mutations). In another particular embodiment, the mutations are present in a heterozygous form (i.e., both alleles carry different HINT1 mutations in a compound heterozygous state). This definition is understood to include the various loss-of function mutations that naturally exist, including, but not limited to, those disclosed herein, as well as synthetic or recombinant mutations produced by human intervention.

In another embodiment, the disclosure provides a nucleic acid probe wherein the nucleotide sequence is a fragment of a nucleic acid sequence derived from a mutant HINT1 gene.

As used herein, "fragment" refers to a nucleotide sequence of at least about 9 nucleotides, typically 15 to 75, or more, wherein the nucleotide sequence comprises at least one mutation for HINT1. The term "fragments or derivatives," as used herein, is defined as portions or variants of a specific nucleic acid or amino acid which retains at least one specific function of the parent sequence. The fragments may be from any location within the nucleic acid or amino acid sequence and may be of any size up to the full sequence size. Derivatives may comprise a mutation, translocation, deletion, duplication, polymorphism, such as a single nucleotide polymorphism, insertion, and others known to a skilled artisan. Derivatives of an amino acid sequence, such as a polypeptide, may contain at least one modification of at least one amino acid residue, such as methylation, phosphorylation, acetylation, or other modifications standard in the art.

In another embodiment, the isolated nucleic acids of the disclosure include any of the above-described sequences or fragments thereof of HINT1 when included in vectors. The term "vector" is used to refer to a carrier nucleic acid molecule into which a nucleic acid sequence can be inserted for introduction into a cell where it can be replicated. Appropriate vectors include cloning vectors and expression vectors of all types, including plasmids, phagemids, cosmids, episomes, and the like, as well as integration vectors. The vectors may also include various marker genes (e.g., antibiotic resistance or susceptibility genes) that are useful in identifying cells successfully transformed therewith. In addition, the vectors may include regulatory sequences to which the nucleic acids of the disclosure are operably joined, and/or may also include coding regions such that the nucleic acids of the disclosure, when appropriately ligated into the vector, are expressed as fusion proteins. Such vectors may also include vectors for use in yeast "two hybrid," baculovirus, and phage-display systems. The vectors may be chosen to be useful for prokaryotic, eukaryotic or viral expression, as needed or desired for the particular application. A great variety of different vectors are now commercially available and otherwise known in the art, and the choice of an appropriate vector is within the ability and discretion of one of ordinary skill in the art.

In yet another embodiment, the disclosure provides a host cell comprising a recombinant vector, according to the disclosure. As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (on the World Wide Web at atcc.org). An appropriate host can be determined by one of skill in the art based on the vector backbone and the desired result. A plasmid or cosmid, for example, can be introduced into a prokaryotic host cell for replication of many vectors. Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

In yet another embodiment, the disclosure provides a method for the preparation of a diagnostic assay to detect the presence of a disease, which is associated with an inherited form of neuromyotonia or to detect a predisposition for an inherited form of neuromyotonia in a subject comprising detecting at least one mutation in the nucleotide position of SEQ ID NO:1 in a tissue sample of the human, wherein the mutation results in a loss of function of HINT1 and wherein the presence of the mutation in both alleles of a subject is indicative for the presence of a disease associated with an inherited form of neuromyotonia.

Neuromyotonia, also known as Isaacs' syndrome, is a form of peripheral nerve hyperexcitability that causes spontaneous muscular activity resulting from repetitive motor unit action potentials of peripheral origin. The three causes of neuromyotonia acquired, paraneoplastic and hereditary. The acquired form is the most common accounting for up to 80 percent of all cases and is suspected to be autoimmune mediated, which is usually caused by antibodies against neuromuscular junction. The disclosure offers a diagnostic test for detecting the inherited form of neuromyotonia.

In yet another embodiment, the disclosure provides a method for the preparation of a diagnostic assay to detect the presence of a peripheral neuropathy or to detect a predisposition for a peripheral neuropathy in a subject, more particularly to detect the presence or to detect a predisposition for an autosomal recessive form of inherited peripheral neuropathy, even more particularly an autosomal recessive form of an axonal peripheral neuropathy associated with neuromyotonia in a subject comprising detecting at least one mutation in the nucleotide position of SEQ ID NO:1 in a tissue sample of the human, wherein the mutation, respectively, results in a loss of function of HINT1 and wherein the presence of a mutation in both alleles of a subject is indicative for the presence of an inherited peripheral neuropathy or with a predisposition to develop an inherited peripheral neuropathy. In a particular embodiment, the presence of a lack of function mutation in HINT1 in only one allele is indicative for the identification of a subject being a carrier of an inherited peripheral neuropathy.

In yet another embodiment, the disclosure provides a diagnostic method for determining if a subject bears a mutant HINT 1 gene encoding a non-functional HINT 1 protein comprising the steps of (1) isolating a tissue sample of the subject, (2) preparing nucleic acids from the tissue sample, (3) amplifying the HINT1 gene or selected regions from the HINT1 gene, (4) determining the DNA sequence of the HINT1 gene or the selected regions thereof and (5) associating the presence of a mutation, which leads to a non-functional HINT1 protein with the presence of an inherited peripheral neuropathy or with the presence of a predisposition to develop an inherited peripheral neuropathy.

In yet another embodiment, the disclosure provides a diagnostic method for determining if a subject bears a mutant HINT1 gene encoding a non-functional HINT1 protein comprising the steps of (1) providing a biological sample of the subject, (2) detecting in the sample a mutant nucleic acid of HINT1 leading to the expression of a non-functional HINT1 protein, and (3) associating the presence of a mutation in both alleles of HINT1 with the presence of an inherited peripheral neuropathy in the subject or with a predisposition of the subject for an inherited peripheral neuropathy.

The diagnostic assay of the disclosure can be useful in the diagnosis of an inherited peripheral neuropathy, more particularly for the diagnosis of an autosomal recessive axonal neuropathy, even more particularly for the diagnosis of an autosomal recessive axonal neuropathy associated with neuromyotonia. The diagnostic assay can also be used to predict if a human is at risk (if a human has a predisposition) to acquire an inherited peripheral neuropathy, more particularly to acquire an autosomal recessive axonal neuropathy, even more particularly to acquire an autosomal recessive axonal neuropathy associated with neuromyotonia. Diagnosis of, for example, inherited cases of these diseases can be accomplished by methods based upon the nucleic acids (including genomic and mRNA/cDNA sequences) and based on the detection of a reduced or lack of HINT1 protein expression (e.g., the detection of HINT1 (or the absence of HINT1 protein) can be measured by using HINT1 specific antibodies). Preferably, the methods and products are based upon the human HINT1 gene, protein or antibodies against the HINT1 protein. As will be obvious to one of ordinary skill in the art, however, the significant evolutionary conservation of large portions of the HINT1 nucleotide and amino acid sequences, even in species as diverse as humans and *C. elegans* and *Drosophila*, allow the skilled artisan to make use of such non-human HINT1-homologue nucleic acids, proteins and antibodies even for applications directed toward human or other mammalian subjects. Thus, for brevity of exposition, but without limiting the scope of the disclosure, the following description will focus upon uses of the human homologues of HINT1 genes and proteins. It will be understood, however, that homologous sequences from other species will be equivalent for many purposes. As will be appreciated by one of ordinary skill in the art, the choice of diagnostic methods of the disclosure will be influenced by the nature of the available biological samples to be tested and the nature of the information required. Assays based upon a subject's genomic DNA may be the preferred methods for diagnostics of HINT1 gene and essentially any nucleate cells may provide a usable sample. When the diagnostic assay is to be based upon nucleic acids from a sample, either mRNA or genomic DNA may be used. When mRNA is used from a sample, many of the same considerations apply with respect to source tissues and the possibility of alternative splicing. That is there may be little or no expression of transcripts unless appropriate tissue sources are chosen or available, and alternative splicing may result in the loss of some information. With either mRNA or DNA, standard methods well known in the art may be used to detect the presence of a particular sequence either in situ or in vitro (see, e.g., Genome Analysis, A laboratory Manual, eds E. D. Green, B. Birren, S. Klapholz, R. M. Myers, P. Hieter, Cold Spring Harbor Laboratory Press, 1997). In a preferred embodiment of the disclosure, the starting nucleic acid represents a sample of DNA isolated from an animal or human patient. This DNA may be obtained from any cell source or body fluid. Non-limiting examples of cell sources available in clinical practice include blood cells, buccal cells, cervico-vaginal cells, epithelial cells from urine, or any cells present in tissue obtained by biopsy. Body fluids include blood, urine, and cerebrospinal fluid. DNA is extracted from the cell source or body fluid using any of the numerous methods that are standard in the art. It will be understood that the particular method used to extract DNA will be chosen as being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction and/or phenol extractions can be used to obtain nucleic acid from cells or tissues, e.g., blood. In a specific embodiment, the cells may be directly used without purification of the target nucleic acid. For example, the cells can be suspended in hypotonic buffer and heated to about 90° C. to 100° C., until cell lysis and dispersion of intracellular components occur, generally about 1 to 15 minutes. After the heating step, the amplification reagents may be added directly to the lysed cells. This direct amplification method may, for example, be used on peripheral blood lymphocytes. The preferred amount of DNA to be extracted for analysis of human genomic DNA is at least 5 pg (corresponding to about 1 cell equivalent of a genome size of $3.10^9$ base pairs). In a particular embodiment, the starting nucleic acid is RNA obtained, e.g., from a cell or tissue. RNA can be obtained from a cell or tissue, according to various methods known in the art and described, e.g., Genome Analysis, A laboratory Manual, eds. E. D. Green, B. Birren, S. Klapholz, R. M. Myers, P. Hieter, Cold Spring Harbor Laboratory Press, 1997. For in situ detection of a mutant nucleic acid sequence of HINT1, a sample of tissue may be prepared by standard techniques and then contacted with a probe, preferably one which is labeled to facilitate detection, and an assay for nucleic acid hybridization is conducted under stringent conditions, which permit hybridization only between the probe and highly or perfectly complementary sequences. In many applications, the nucleic acids are labeled with directly or indirectly detectable signals or means for amplifying a detectable signal. Examples include radiolabels, luminescent (e.g., fluorescent) tags, components of amplified tags such antigen-labeled antibody, biotin-avidin combinations, etc. The nucleic acids can be subject to purification, synthesis, modification, sequencing, recombination, incorporation into a variety of vectors, expression, transfection, administration or methods of use disclosed in standard manuals such as Genome Analysis, A laboratory Manual, eds E. D. Green, B. Birren, S. Klapholz, R. M. Myers, P. Hieter, Cold Spring Harbor Laboratory Press, 1997 or that are otherwise known in the art. Because many mutations in genes that cause diseases detected to date consist of a single nucleotide substitution, high stringency hybridization conditions will be required to distinguish normal sequences from most mutant sequences. A significant advantage of the use of either DNA or mRNA is the ability to amplify the amount of genetic material using the polymerase chain reaction (PCR), either alone (with genomic DNA) or in combination with reverse transcription (with mRNA to produce cDNA). Other nucleotide sequence amplification techniques may be used, such as ligation-mediated PCR, anchored PCR and enzymatic amplification as will be understood by those skilled in the art. Other methods which can be used to determine HINT1 expression levels include Northern blotting, quantitative PCR and RT-PCR. Sequence alterations may also generate fortuitous restriction enzyme recognition sites, which are revealed by the use of appropriate enzyme digestion, followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized, for example, under UV light in the presence of ethidium bromide, after gel electrophoresis. Genetic testing based on DNA sequence differences may be achieved by detection of alteration in electrophoretic mobility of DNA fragments in gels. Small sequence deletions and insertions can be visualized by high-resolution gel electrophoresis of single stranded DNA, or as changes in the migration pattern of DNA heteroduplexes in non-denaturing gel electrophoresis. Alternatively, a single base substitution mutation may be detected based on differential PCR product length in PCR. The PCR products of the normal and mutant gene may be differentially detected in acrylamide gels. Nuclease protection assays (S1 or ligase-mediated) also reveal sequence changes at specific locations. Alternatively, to confirm or detect a polymorphism resulting in restriction mapping changes, ligated PCR, allele specific oligonucleotide probes (ASOs), REF-SSCP chemical cleavage, endonuclease cleavage at mismatch sites or SSCP may be used. Both REF-SSCP and SSCP are mobility shift assays, which are based upon the change in conformation due to mutations. DNA fragments may also be visualized by methods in which the individual DNA samples are not immobilized on membranes. The probe and target sequences may be in solution or the probe sequence may be immobilized. Autoradiography, radioactive decay, spectrophotometry and fluorometry may also be used to identify specific individual genotypes. Mutations in HINT1 can also be detected by direct nucleotide sequencing (e.g., by sequencing exons, introns, or untranslated sequences). Methods for nucleotide sequencing are well known in the art. Fragments of the disclosed alleles of HINT1 are sufficiently long for use as specific hybridization probes for detecting endogenous alleles, and particularly to distinguish the disclosed mutant alleles from the wild-type alleles. Preferred fragments are capable of hybridizing to the corresponding mutant allele under stringency conditions characterized by a specific hybridization buffer. In any event, the fragments are necessarily of length sufficient to be unique to the corresponding allele; i.e., has a nucleotide sequence at least long enough to define a novel oligonucleotide, usually at least about 14, 16, 18, 20, 22, or 24 bp in length, though such fragment may be joined in sequence to other nucleotides, which may be nucleotides which naturally flank the fragment. For example, where the subject nucleic acids are used as PCR primers or hybridization probes, the subject primer or probe comprises an oligonucleotide complementary to a strand of the mutant or rare allele of length sufficient to selectively hybridize with the mutant or rare allele. Generally, these primers and probes comprise at least 16 bp to 24 bp complementary to the mutant or rare allele and may be as large as is convenient for the hybridizations conditions. In some cases where the critical mutation in HINT1 is a deletion of wild-type sequence, useful primers/probes require wild-type sequences flanking (both sides) the deletion with at least 2, usually at least 3, more usually at least 4, most usually at least 5 bases. Where the mutation is an insertion or substitution, which exceeds about 20 bp, it is generally not necessary to include wild-type sequence in the probes/primers. For insertions or substitutions of fewer than 5 bp, preferred nucleic acid portions comprise and flank the substitution/insertion with at least 2, preferably at least 3, more preferably at least 4, most preferably at least 5 bases. For substitutions or insertions from about 5 bp to about 20 bp, it is usually necessary to include both the entire insertion/substitution and at least 2, usually at least 3, more usually at least 4, most usually at least 5 basis of wild-type sequence of at least one flank of the substitution/insertion. In a particular embodiment, deletions are detected in the HINT1 gene.

In yet another particular embodiment, the disclosure provides a diagnostic kit for diagnosing a hereditary peripheral neuropathy, more particularly an autosomal recessive form of a hereditary axonal peripheral neuropathy, even more particularly an autosomal recessive form of a hereditary axonal peripheral neuropathy associated with neuromyotonia. In a particular embodiment such a diagnostic kit comprises at least two primers, wherein one primer is specific to a sense HINT1 nucleic acid and another primer is specific to an antisense HINT1 nucleic acid. In a particular embodiment, the at least two primers are selected from the sequence depicted as SEQ ID NO:1. It is appreciated that all the essential materials and/or reagents required for detecting a HINT1 nucleic acid sequence in a sample may be assembled together in a kit. This generally will comprise a probe or primers designed to hybridize specifically to individual nucleic acids of interest in the practice of the disclosure, specifically SEQ ID NO:1. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

The wording "stringent hybridization conditions" is a term of art understood by those of ordinary skill in the art. For any given nucleic acid sequence, stringent hybridization conditions are those conditions of temperature, chaotrophic salts, pH and ionic strength, which will permit hybridization of that nucleic acid sequence to its complementary sequence and not to substantially different sequences. The exact conditions, which constitute "stringent" conditions, depend upon the nature of the nucleic acid sequence, the length of the sequence, and the frequency of occurrence of subsets of that sequence within other non-identical sequences. By varying hybridization conditions from a level of stringency at which non-specific hybridization conditions occurs to a level at which only specific hybridization is observed, one of ordinary skill in the art can, without undue experimentation, determine conditions which will allow a given sequence to hybridize only with complementary sequences. Hybridization conditions, depending upon the length and commonality of a sequence, may include temperatures of 20° C. to 65° C. and ionic strengths from 5× to 0.1×SSC. Highly stringent hybridization conditions may include temperatures as low as 40° C. to 42° C. (when denaturants such as formamide are included) or up to 60° C. to 65° C. in ionic strengths as low as 0.1×SSC. These ranges, however, are only illustrative and, depending upon the nature of the target sequence, and possible future technological developments, may be more stringent than necessary.

In yet another embodiment, the disclosure provides a method for the preparation of a diagnostic assay to detect the presence or a predisposition to a peripheral neuropathy, more particularly an autosomal recessive axonal neuropathy associated with neuromyotonia, in a human comprising detecting at least one mutation in the nucleotide sequence of SEQ ID NO:1 in a tissue sample of the human, wherein the mutation is derived from Table 1 and wherein the presence of a mutation in both alleles is indicative of a predisposition or the presence of a peripheral neuropathy, more particularly an autosomal recessive axonal peripheral neuropathy with neuromyotonia.

In a particular embodiment when a diagnostic assay is to be based upon the detection of HINT1 protein, and more particularly on the quantification of HINT1 protein, a variety of approaches are possible. Such diagnostic tests may employ antibodies, which specifically bind to the HINT1 protein. The levels of anti-HINT1 in a sample obtained from a test subject (visualized by, for example, radiolabeling, ELISA or chemiluminescence) may be compared to the levels of binding to a control sample (i.e., the latter known not to carry mutations in the HINT 1 alleles). Other methods to detect HINT 1 with an antibody against HINT1 (preferentially labeled with, for example, a radioactive molecule, a fluorescent molecule) include fluorescent activated cell sorting technology, Western blotting and immunoprecipitation. Such antibody diagnostics may also be used for in situ immunohistochemistry using biopsy samples of tissues obtained antemortem or postmortem or may be used with fluid samples such a cerebrospinal fluid or with peripheral tissues such as white blood cells.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting and are provided to illustrate certain particular features and/or embodiments. These examples should not be construed to limit the disclosure to the particular features or embodiments disclosed.

EXAMPLES

Figure 1:
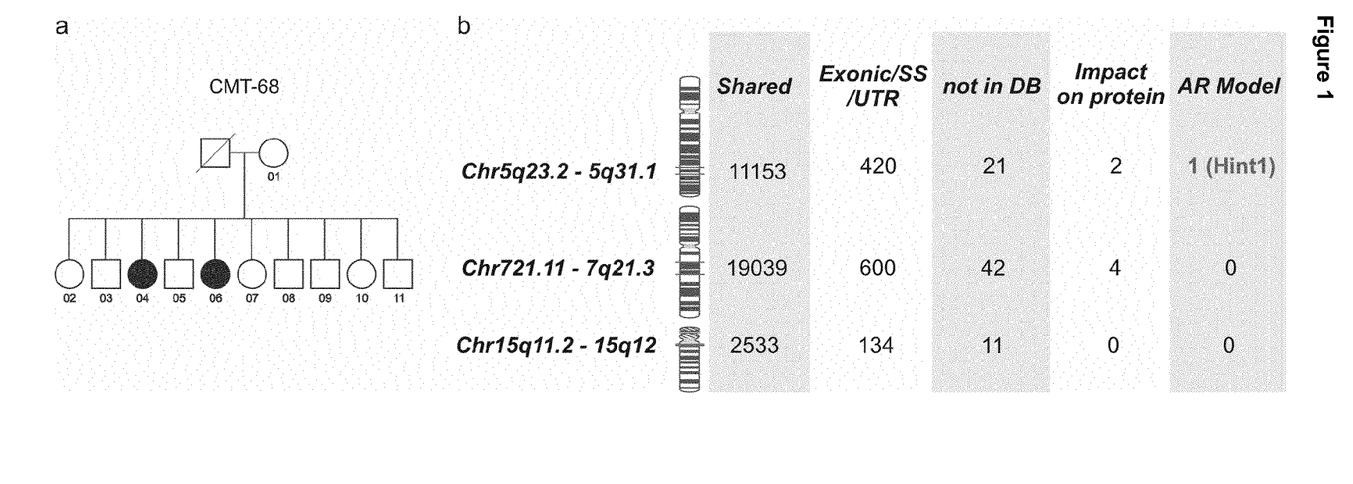
FIG. 1: Panel A. Pedigree CMT-68; Panel B. The three candidate genomic regions identified by the linkage analysis of family CMT-68. The table indicates the shared nucleotide variants between the two affected individuals, the portion located in exonic and untranslated (UTR) coding regions, and the number of variants not reported in databases (DB).
Figure 2:
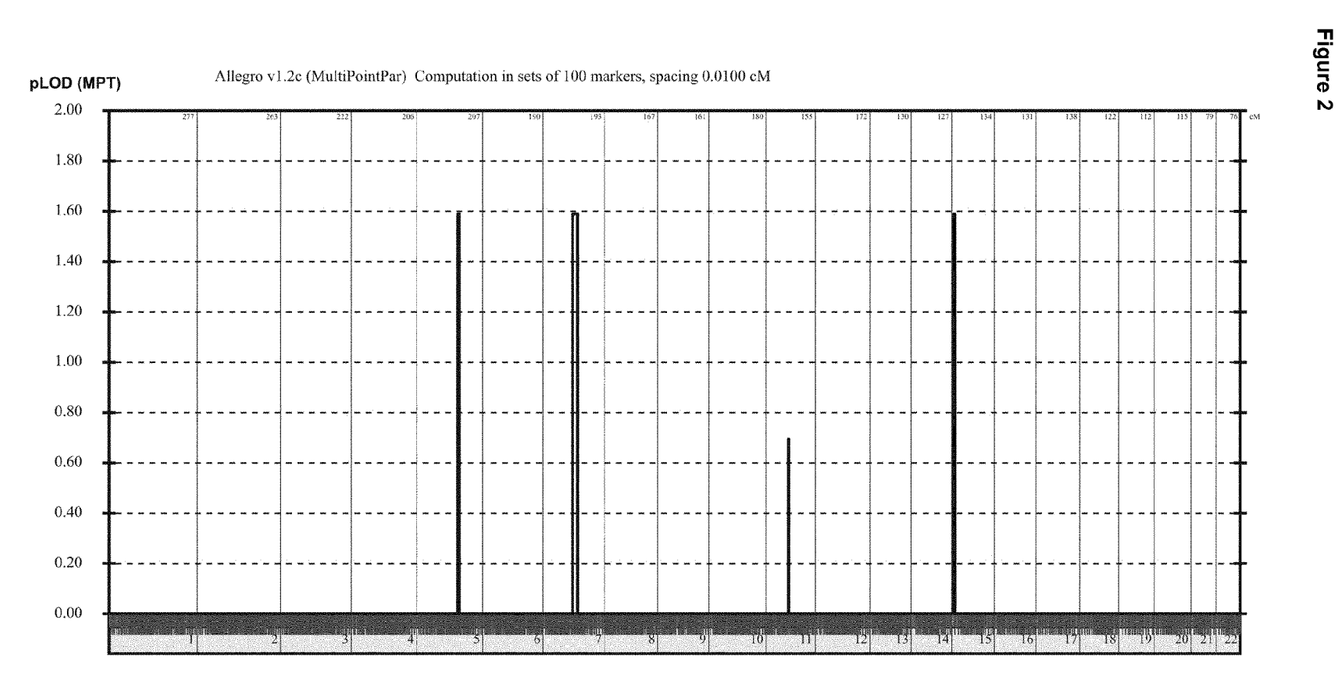
FIG. 2: Results from parametric multipoint linkage analysis using the Allegro v1.2c software.

1. Identification of Mutations in the Histidine Triad Nucleotide Binding Protein 1 in Patients with a Hereditary Peripheral Neuropathy We performed whole genome SNP genotyping of a Belgian family (CMT-68) diagnosed with autosomal recessive-Charcot Marie Tooth disease (AR-CMT) associated with neuromyotonia (FIG. 1a). Initial homozygosity mapping revealed no regions >1 Mb in size suggesting compound heterozygosity for a recessive disease locus. Subsequent parametric linkage analysis yielded three plausible disease loci on chromosome 5 (10 Mb), 7 (18 Mb) and 15 (1.5 Mb) (FIGS. 1b, 2). Haplotype analysis confirmed segregation of all three loci. Whole-genome sequencing of the two affected sibs revealed 35231 shared variation in these three regions. Subsequent filtering identified two heterozygous nucleotide variations, c.110G>C (R37P) and c.250T>C (C84R), in exon 1 and 2 of histidine triad nucleotide binding protein 1 (HINT1) located on chromosome 5q31.1 (FIG. 1). Segregation was confirmed through Sanger sequencing of HINT1 in all family members. The R37P and C84R variants were absent from 270 ethnically matched control individuals.

Subsequently, we performed an unbiased screening in 200 AR-CMT index patients. We found the two already identified and three new sequence variations in a total of ten families. Eight families were homozygous for R37P, they were of Croatian (CMT-419, PN-1334), Serbian (PN1281a), Bulgarian (CMT-732), Turkish (CMT-162, CMT-579, CMT-1239) and American (CMT-1315) origin. Isolated Italian patient (CMT-726.01) was homozygous for H112N, Turkish patient (CMT-1265.01) for W123X.

All patients carrying HINT1 mutations were diagnosed with motor greater than sensory axonal neuropathy associated with neuromyotonia, a syndrome of delayed muscle relaxation upon voluntary contraction resulting from a disease of the peripheral nerve rather than muscle[2]. Peripheral neuropathy with neuromyotonia is characterized by clinical action myotonia of the hands and/or spontaneous high-frequency motor unit potentials on concentric needle EMG consistent with neuromyotonic and myokimic discharges.

In the light of these findings we further extended our mutation screening to patients with a similar phenotype. In 20 additional index patients we identified mutations in HINT1 gene. The majority carried similar mutations, as described herein, before but also new sequence variations were found in a Belgian patient (PN-1899) compound heterozygous for H51R/C84R and a family of Chinese ancestry (CMT-1350) that was previously reported clinically[2] and carries the compound heterozygous Q62X/G93D mutations.

Segregation of mutations was confirmed in all available family members and additional ethnically matched controls were analyzed. The heterozygous variant R37P was found in 3/200 Serbian control individuals. Furthermore, H112N and R37P were reported as heterozygous variants in the NHLBI GO Exome Sequencing Project (on the World Wide Web at esp.gs.washington.edu/drupal/), H112N and R37P each in 1/7020 alleles from European American population and R37P in 1/3737 from African American population. Altogether, the estimated carrier-frequency of R37P in the control European/American population is at least 1:1500. In silico analysis of mutations with Polyphen2 software showed that all, except R37P, targeted highly conserved amino acid residues.

Due to the reoccurrence of the R37P, C84R and H112N mutations in various families, we performed STR and SNP based haplotype analysis to investigate the possibility of a common ancestry. In case of all three mutations, we identified common haplotype shared by all affected individuals. For the R37P mutation, the core haplotype encompassed a region of 1 Mb in size.

An overview of the different mutations identified in HINT1 is depicted in Table 1.

TABLE 1

7 different mutations were identified in the HINT1 gene in 29 families with disease carriers of a hereditary peripheral neuropathy.

| Patient Genotypes | | | Number families |
|---|---|---|---|
| AA change | Nucleotide change | exon | (number patients) |
| Arg37Pro/Arg37Pro | c.110G > C/c.110G > C | 1 | 22 (33) |
| Arg37Pro/Cys84Arg | c.110G > C/c.250T > C | 1/3 | 1 (2) |
| Arg37Pro/His112Asn | c.110G > C/c.334C > A | 1/3 | 1 (2) |
| His51Arg/Cys84Arg | c.152A > G/c.250T > C | 2/3 | 1 (1) |
| Gln62X/Gly93Asp | c.184C > T/c.278G > A | 2/3 | 1 (2) |
| His112Asn/His112Asn | c.334C > A/c.334C > A | 3 | 2 (2) |
| Trp123X/Trp123X | c.334C > A/c.334C > A | 3 | 1 (1) |
| 7 different mutations | | | 29 |

2. Determination of Loss of Function of the Identified HINT1 Mutations

Some of the mutated residues we identified (H51, C84, H112 and W123) are known to be crucial for HINT1 enzymatic activity. Two of them are targeting the highly conserved H51 and H112 residues[4]. The later histidine, when mutated to either alanine or asparagine, results in an enzymatically "dead" protein[4,7]. Mutations in residues W123 and C84 lead to reduced activity and in case of the first one to also change in substrate recognition[8,9]. To investigate the effect of the neuropathy-causing mutations on HINT1 protein function, we performed in vivo complementation assay using a yeast strain deficient for the HINT1 orthologue hnt1 (strain BY8-5c). Despite normal growth at standard conditions, this strain is incapable to grow under restrictive conditions (39° C. on galactose-containing media)[4]. Transformation of the hnt1 deficient strain, with either the yeast hnt1 or wild-type human HINT1, restored growth of the recombinants under restrictive conditions, confirming the functional homology between both proteins. Conversely, the C84R mutations showed a severely compromised complementation capacity, while the R37P, H51R, H112N and W123X mutations were completely unable to support yeast viability.

3. Determination of HINT1 Protein Levels in Patient Samples Carrying HINT1 Mutations In a next step we checked HINT1 levels in lymphoblast cultures derived from patients. Surprisingly, very low levels of protein were detected for patients with either R37P/R37P or R37P/C84R mutations. To determine if the lack of protein in these patients is due to protein degradation, we treated lymphoblast cultures with MG132 proteasome inhibitor, and this led to accumulation of HINT1 protein over time, suggesting that these mutations impair protein stability in vivo.

Taking together, these data show that the peripheral neuropathy due to HINT 1 mutations is caused by a lack of functional HINT1, e.g., by loss of activity and/or by proteasomal degradation of the mutant protein.

Materials and Methods

1. Patient Cohort

We have ascertained a cohort of 200 unrelated index patients diagnosed with autosomal recessive demyelinating or axonal CMT. Another cohort comprised of 30 patients having a diagnosis of peripheral neuropathy with neuromyotonia.

2. Whole Genome SNP Genotyping, Homozygosity Mapping and Linkage Analysis

DNA of 11 individuals from family CMT-68 was isolated from peripheral blood samples, according to standard procedures. Whole genome SNP genotyping was performed with Illumina Human660W-Quad platform. Homozygosity scan was performed with PLINK program (Purcell S et al. (2007) *Am. J. Hum. Genet.* 81, 559-575), homozygous regions were called when greater than ≥1 Mb and contained ≥100 SNPs. Multipoint parametric linkage analysis was performed with easyLINKAGE program package (Hoffman K and Lindner TH (2005) *Bioinformatics* 21, 3565-3567) under assumption of autosomal recessive model, equal female/male recombination rates, a 0.0001 disease frequency and only SNPs distant from each other by 0.001 cM were analyzed. Regions with LOD scores ≥0.6 were checked for co-segregation of the haplotype with the disease.

3. Whole Genome Sequencing

The genomes of two affected individuals from family CMT-68 were sequenced by Complete Genomics, Inc. (on the World Wide Web at .completegenomics.com/). Primary analysis including sequence mapping, assembly to NCBI36.1 reference genome and variant calling was performed by CGI. Provided data included variant calls (together with functional annotation), copy number variations (CNV) and structural variations (SV) calls files, as well as the alignment and coverage files. Subsequent data modifications, annotation and filtering were performed with GenomeComb tools (on the World Wide Web at genomecomb.sourceforge.net/index.html). As control genomes, we used 90 sequenced control samples available at the VIB Department of Molecular Genetics and public databases like dbSNP129, data from 1000 Genome Project and 69 genomes of HapMap individuals sequenced by CGI (on the World Wide Web at ftp2.completegenomics.com/YRI_trio/ASM_Build37/NA19240/).

4. Mutation Analysis

All 3 coding exons and exon-intron boundaries of HINT1 were PCR-amplified on total genomic DNA isolated from peripheral blood samples of CMT patients and control individuals. Primers were designed with Primer3 software (Rozn S. and Skaletsky H. (2000) *Methods Mol. Biol.* 132, 365-386). Purified with the Exonuclease I-Shrimp Alkaline Phosphatase enzymes (USB, Cleveland, USA) PCR products were bi-directionally sequenced using the BIGDYE® Terminator v3.1 Cycle Sequencing Kit (Applied Biosystems, Foster City, USA). Fragments were electrophoretically separated on an ABI3730x1 DNA Analyzer (Applied Biosystems, Foster City, USA). Trace files were analyzed with the SEQMAN® II (DNASTAR, Inc., Madison, USA) program. Mutations were described according to the HGVS nomenclature (on the World Wide Web at .hgvs.org/mutnomen) with nucleotide numbering based on the published online protein (NP_005331.1) and mRNA (NM_005340.5) sequences of HINT1 (on the World Wide Web at .ncbi.nlm.nih.gov). All sequence variants were confirmed by an independent PCR and re-sequencing of the original or newly obtained DNA samples. Segregation analysis of the mutations with the disease phenotype was performed in all available family members. Ethnically matched control individuals were screened for all mutations identified; for exon1 (Arg37Pro) in total of 939 control individuals (270 Belgian, 160 Turkish, 192 Bulgarian, 42 Turkish-Bulgarian, 200 Serbian, 75 Gypsy), for exon 2 mutations (His51Arg, Gln62X) 270 Belgian individuals, for exon 3 (Cys84Arg, Gly93Asp, His112Asn, Trp123X) in total 585 controls (140 Turkish, 270 Belgian, 84 Bulgarian, 91 Italian). In silico prediction of the functional effect of mutations was performed with PolyPhen-2 algorithm (on the World Wide Web at genetics.bwh.harvard.edu/pph2/index.shtml).

5. Haplotype Sharing and Paternity Testing

We performed haplotype sharing analysis between families with common mutation using eight short tandem repeat (STR) markers (D5S1495, D5S642, D5S2120, D5S809, D5S666, D5S2110, D5S2057, D5S2117) surrounding HINT1 region. We subsequently performed Sequenom genotyping of single nucleotide polymorphisms (SNPs) both surrounding and within the gene region. Paternity was examined with 15 STRs distributed throughout the genome (ATA38A05, D1S1646, D1S1653, D1S1360, D2S2256, D3S3037, D4S2382, D4S3240, D7S509, D8S1759, D9S1118, D12S1056, D12S2082, D16S2619 and GATA152H04). STRs were first PCR-amplified with fluorescently-labeled primer pairs (sequences are available on the World Wide Web at .ncbi.nlm.nih.gov), fragments were then mixed with a formamide and GENESCAN® 500 LIZ® Size Standard (Applied Biosystems, Foster City, USA) (ratio 1:30) and size-separated on an ABI3730x1 DNA Analyzer. Genotyping results were analyzed with Local Genotype Viewer, an in-house developed software program (on the World Wide Web at .vibgeneticservicefacility.be/). PCR primers and extension primers for Sequenom analysis, were designed with the MASSARRAY® Designer Software. First, we performed multiplex PCR amplification of fragments specific for each SNP and primer extension process—iPLEX Gold assay allowed differentiation between alleles based on the mass of extension products.

6. Lymphoblastoid Cell Lines

Total blood samples obtained from either patients or control individuals were mixed with 15 ml of Ficol Paque and next centrifuged for 10 min. Following washing step, lymphocytes were transformed with Epstein-Barr virus and incubated at 37° C. for 2 hrs. Cells were then centrifuged and pellet was resuspended in 4 ml of RPMI complete medium with 1% phytohaemagglutinin. Subsequently, cells were seeded on a 24-well plate and incubated at 37° C., 5% $CO_2$ for minimum of 3 days.

7. Cloning and Site Directed Mutagenesis

Human HINT1 transcript was PCR-amplified from HeLa and HEK293 cDNA mix (ratio—1:1) and yeast hnt1 genomic sequence—from BY2 genomic DNA using specially designed Gateway cloning system-compatible primers with attB-flanking sequences with Platinum DNA High Fidelity Taq Polymerase (Invitrogen). All constructs were then generated by Gateway recombination system (Invitrogen) according to manufacturer's instructions. Entry vector pDONR221 was purchased from Invitrogen and destination vector for *Saccharomyces cerevisiae* expression—from Addgene (on the World Wide Web at .addgene.org/yeast-gateway/). Five HINT1 mutations (Arg37Pro, His51Arg, Cys84Arg, His112Asn, Trp123X) were introduced by site-directed-mutagenesis into selected clone (hHINT1-pDONR221) with specially designed primers. Sequences of all primers used are available upon request.

8. Cell Culture Conditions and Treatments

Lymphoblastoid cell lines derived from patients and control individuals were cultivated at 37° C., 5% $CO_2$ in RPMI1640 medium (Invitrogen) supplemented with 15% fetal calf serum, sodium pyruvate, glutamine and penicillin/streptomycin. Cells at the density of $1 \times 10^6$ cells/ml were treated with either 10 µM MG132 (Calbiochem) proteasome inhibitor or with respective amount of DMSO and incubated at standard conditions. After 0, 4 and 8 hours—1 ml sample was taken for further western blotting analysis.

9. Protein Isolation and Western Blotting

Tissues of an adult mouse were separated and flash frozen in liquid nitrogen and stored at −80° C. and later used for protein isolation. They were crushed in a douncer and lysed with E1a buffer (Goethals S et al. (2010) *Glia* 58, 1701-1709) supplemented with a Complete Protease Inhibitor Cocktail tablet (Roche, Basel, Switzerland). Supernatant protein concentrations were determined using Bradford Assay (Bio-Rad). Equal amounts of proteins were denatured for 5 min at 95° C. in SDS loading buffer (5× solution: 250 mM Tris-HCl, pH 6.8, 10% SDS, 30% glycerol, 0.02% bromophenol blue) supplemented with DTT up to the final concentration of 100 mM. Samples were size-separated on NuPAGE 4% to 12% SDS-polyacrylamide gels (Invitrogen) and transferred to nitrocellulose membranes. Membranes were immunoblotted with polyclonal rabbit anti-HINT1 antibody (1:1000, Sigma Aldrich), equal protein loading was proved with either mouse monoclonal anti-β-actin antibody (1:20,000, Sigma-Aldrich) for cell lysates or mouse monoclonal anti-GAPDH antibody (1:20,000, Sigma-Aldrich) for mouse tissues. Secondary antibodies used were horseradish peroxidase-conjugated to mouse, rabbit and IgG1-epitope (Jackson Immuno Research Laboratories Inc.). Western blot results were then visualized with Amersham ECL Plus (GE Healthcare). Band intensity was quantified using the ImageJ software (on the World Wide Web at rsbweb.nih.gov/ij/). Statistical significance of the differences in the expression levels of HINT1 protein in different mouse tissues was tested using a two-tailed t-test.

10. Yeast Spot Assay

Yeast pAG415 constructs containing wild-type (WT) human HINT1 (hHINT1), yeast hnt1 or any of the five mutants: Arg37Pro, His51Arg, Cys84Arg, His112Asn, Trp123X, or empty vector were transformed Gietz and Schiestl (2007) *Nat. Protoc.* 2, 31-34) into haploid hnt1 deletion strain (hnt1Δ)—BY8-5c (Bieganowski P et al. (2002) *J. Biol. Chem.* 277, 10852-10860). Transformants were initially grown on synthetic minimal glucose medium without leucine (SD-Glu-Leu) at 30° C. Liquid cultures were inoculated with selected clones and grown overnight. Next day, absorbance was measured at 600 nm and cultures were diluted to 0.1, 0.02, 0.004, 0.0008. Subsequently, 5 ul of each dilution was spotted either on SD-Glu-Leu plates or synthetic minimal galactose medium without leucine (SD-Gal-Leu) and incubated either at 30° C. or at 39° C. for 5 days, respectively.

11. Yeast Growth Curve Determination

Liquid cultures were inoculated with selected clones (WT-hHINT1, WT-yHINT1, Arg37Pro, His51Arg, Cys84Arg, His112Asn, Trp123X, empty vectors: pAG415, pAG415-GFP) and grown overnight. Then absorbance was measured at 600 nm and cultures were diluted to the absorbance of 0.08 in either SD-Glu-Leu, SD-Gal-Leu liquid medium and 250 ul of each suspension was incubated on a special plate in Bioscreen for 55 hrs at 39° C. with shaking every 30 sec for 3 sec, growth was monitored every 30 min.

REFERENCES

1. Skre, H. Genetic and clinical aspects of Charcot-Marie-Tooth's disease. *Clin. Genet.* 6, 98-118 (1974).
2. Hahn, A. F., Parkes, A. W., Bolton, C. F., & Stewart, S. A. Neuromyotonia in hereditary motor neuropathy. *J. Neurol. Neurosurg. Psychiatry* 54, 230-235 (1991).
3. Brenner, C. Hint, Fhit, and GalT: function, structure, evolution, and mechanism of three branches of the histidine triad superfamily of nucleotide hydrolases and transferases. *Biochemistry* 41, 9003-9014 (2002).
4. Bieganowski, P. et al. Adenosine monophosphoramidase activity of Hint and Hnt1 supports function of Kin28, Cell, and Tfb3. *J. Biol. Chem.* 277, 10852-10860 (2002).
5. Chou, T. F. & Wagner, C. R. Lysyl-tRNA synthetase-generated lysyl-adenylate is a substrate for histidine triad nucleotide binding proteins. *J. Biol. Chem.* 282, 4719-4727 (2007).
6. Weiske, J. & Huber, O. The histidine triad protein Hint1 interacts with Pontin and Reptin and inhibits TCF-beta-catenin-mediated transcription. *J. Cell Sci.* 118, 3117-3129 (2005).
7. Weiske, J. & Huber, O. The histidine triad protein Hint1 triggers apoptosis independent of its enzymatic activity. *J. Biol. Chem.* 281, 27356-27366 (2006).
8. Parks, K. P. et al. Altered specificity of Hint-W123Q supports a role for Hint inhibition by ASW in avian sex determination. *Physiol Genomics* 20, 12-14 (2004).
9. Ozga, M., Dolot, R., Janicka, M., Kaczmarek, R., & Krakowiak, A. Histidine triad nucleotide-binding protein 1 (HINT-1) phosphoramidase transforms nucleoside 5'-O-phosphorothioates to nucleoside 5'-O-phosphates. *J. Biol. Chem.* 285, 40809-40818 (2010).

The invention claimed is:

1. An isolated cDNA encoding a mutant histidine triad nucleotide-binding protein 1 (HINT1) polypeptide, the HINT1 polypeptide comprising SEQ ID NO: 2 comprising mutation Arg37Pro.

2. A diagnostic kit comprising:
   the cDNA of claim 1, and
   control primer sequences.

3. An isolated recombinant vector comprising the cDNA of claim 1.

4. An isolated host cell comprising the recombinant vector of claim 3.

* * * * *